United States Patent
Watanabe et al.

(10) Patent No.: US 10,010,698 B2
(45) Date of Patent: Jul. 3, 2018

(54) CATHETER

(71) Applicant: TERUMO KABUSHIKI KAISHA, Shibuya-ku, Tokyo (JP)

(72) Inventors: Kouhei Watanabe, Fujinomiya (JP); Hideto Nagata, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/705,646

(22) Filed: May 6, 2015

(65) Prior Publication Data
US 2015/0231360 A1    Aug. 20, 2015

Related U.S. Application Data

(63) Continuation of application No. PCT/JP2012/079341, filed on Nov. 13, 2012.

(51) Int. Cl.
*A61M 25/00*    (2006.01)

(52) U.S. Cl.
CPC ........ *A61M 25/008* (2013.01); *A61M 25/005* (2013.01); *A61M 25/0053* (2013.01); *A61M 25/0054* (2013.01)

(58) Field of Classification Search
CPC .......... A61M 25/0012; A61M 25/0013; A61M 25/005; A61M 25/0051; A61M 25/0052;
(Continued)

(56) References Cited

U.S. PATENT DOCUMENTS

| 5,911,715 A | 6/1999 | Berg et al. |
| 6,193,705 B1 * | 2/2001 | Mortier ............ A61M 25/0041 604/264 |

(Continued)

FOREIGN PATENT DOCUMENTS

| JP | 2001-190681 A | 7/2001 |
| JP | 2004-512150 A | 4/2004 |

(Continued)

OTHER PUBLICATIONS

International Search Report (PCT/ISA/210) dated Jan. 29, 2013, by the Japanese Patent Office as the International Searching Authority for International Application No. PCT/JP2012/079341.

(Continued)

*Primary Examiner* — Bhisma Mehta
*Assistant Examiner* — Jenna Zhang
(74) *Attorney, Agent, or Firm* — Buchanan Ingersoll & Rooney PC

(57) ABSTRACT

A shaft of a catheter is disclosed, the shaft has a thin portion, which constitutes a distal side of the shaft, a thick portion which is provided further on a proximal side than the thin portion, and a tapered portion which is provided between the thin portion and the thick portion. The tapered portion is formed more flexibly than the thick portion. The thick portion has a first thick portion and a second thick portion which is provided between the tapered portion and the first thick portion. The second thick portion has a smaller outer diameter than the outer diameter of a proximal end of the tapered portion and the outer diameter of the first thick portion, and is formed more flexibly than the first thick portion.

18 Claims, 5 Drawing Sheets

(58) Field of Classification Search
CPC .......... A61M 25/0053; A61M 25/0054; A61M 25/008; A61M 2025/0081
USPC .......................................... 604/523–527, 529
See application file for complete search history.

(56) References Cited

U.S. PATENT DOCUMENTS

| | | | |
|---|---|---|---|
| 6,548,010 B1* | 4/2003 | Stivland | A61M 25/0014 156/158 |
| 6,663,614 B1 | 12/2003 | Carter | |
| 2002/0156459 A1 | 10/2002 | Ye et al. | |
| 2002/0156460 A1 | 10/2002 | Ye et al. | |
| 2004/0064130 A1 | 4/2004 | Carter | |
| 2004/0243102 A1* | 12/2004 | Berg | A61M 25/0013 604/525 |
| 2006/0089618 A1 | 4/2006 | McFerran et al. | |
| 2009/0012481 A1* | 1/2009 | Davey | A61M 25/0021 604/265 |
| 2009/0264770 A1 | 10/2009 | Liu et al. | |
| 2010/0094258 A1 | 4/2010 | Shimogami et al. | |
| 2010/0217372 A1* | 8/2010 | Lentz | A61F 2/95 623/1.11 |
| 2014/0142551 A1* | 5/2014 | Nagata | A61M 25/0012 604/524 |

FOREIGN PATENT DOCUMENTS

| | | | |
|---|---|---|---|
| JP | 2004-154195 | A | 6/2004 |
| JP | 2004154195 | A * | 6/2004 |
| JP | 2004-526529 | A | 9/2004 |
| JP | 2005-501613 | A | 1/2005 |
| JP | 2007-000358 | A | 1/2007 |
| JP | 2008-517652 | A | 5/2008 |
| JP | 2008-229160 | A | 10/2008 |
| JP | 2010-88833 | A | 4/2010 |
| JP | 2012-196389 | A | 10/2010 |
| JP | 2012-029872 | A | 2/2012 |
| JP | 2014-097089 | A | 5/2014 |
| JP | 2014-097090 | A | 5/2014 |
| WO | 02-36194 | A2 | 5/2002 |
| WO | 02-085441 | A1 | 10/2002 |
| WO | 03-020353 | A1 | 3/2003 |
| WO | WO 2006/047169 | A1 | 5/2006 |

OTHER PUBLICATIONS

Office Action dated Jan. 13, 2016, by the Japanese Patent Office in corresponding Japanese Patent Application No. 2014-546748. (2 pages).

European Search Report dated Jun. 27, 2016, by the European Patent Office, in corresponding European Patent Application No. 12888296.6 (7 pages).

Office Action dated Dec. 21, 2016, by the Chinese Patent Office in corresponding Chinese Patent Application No. 201280075601.8. (6 pages).

Office Action (Communication) dated Dec. 16, 2016, by the European Patent Office in corresponding European Patent Application No. 12888296.6. (3 pages).

* cited by examiner

CATHETER

CROSS-REFERENCES TO RELATED APPLICATIONS

This application is a continuation of International Application No. PCT/JP2012/079341 filed on Nov. 13, 2012, the entire content of which is incorporated herein by reference.

TECHNICAL FIELD

The present disclosure generally relates to a catheter.

BACKGROUND DISCUSSION

A catheter can be used for, for example, injecting a medicine for treatment or injecting a contrast agent for diagnosis by being inserted into a blood vessel or a lumen in a living body and making a distal portion of the catheter reach a target part. For this reason, it can be necessary for a shaft, which constitutes a main body of the catheter, to be selectively advanced along a guide wire which is previously introduced into a blood vessel or a lumen in a living body which is complicatedly branched in the body.

In recent years, small cancers have been found in a more peripheral area due to the development of diagnostic devices. Therefore, there are more cases in which the catheter needs to be advanced into the peripheral meandering blood vessel than before. Accordingly, smooth accessibility can be necessary for the catheter without applying a burden on the blood vessel. The distal end of the catheter is preferably as flexible as possible in order to enhance flowability with respect to curvature of the peripheral blood vessel. Meanwhile, it is also necessary that pushing force from the operator side be effectively transmitted to a distal side in order to make the catheter travel within the blood vessel. Accordingly, a catheter of which the distal portion is flexible and which becomes hard toward the operator side from the distal end of the catheter can be required.

In order to meet the demand, in the related art, a catheter is disclosed, which includes a shaft having a thin portion on a distal side, a thick portion on a proximal side, and a tapered portion which is provided between the thin portion and the thick portion and of which the outer diameter is reduced toward the distal side of the catheter (for example, refer to JP-A-2012-29872). According to the catheter provided with such a configuration, high flexibility on the distal side can be obtained and appropriate hardness on the operator side can be secured since the outer diameter of the shaft is reduced toward the distal portion from a proximal portion of the catheter.

SUMMARY

In a catheter, it can be preferable that favorable operability is obtained such that the catheter can be inserted into a blood vessel and the catheter can travel relatively smoothly within the blood vessel. In addition, a smooth transmission of pushing force from the operator side to the distal side of the catheter can contribute to an improvement in the operability.

The present disclosure has been made in consideration of such a problem, and a catheter is disclosed in which flexibility is changed along an axial direction of a shaft of the catheter, and which can easily transmit pushing force from the operator side to the distal side, and therefore improving operability.

In accordance with an exemplary embodiment, a catheter is disclosed with a tubular shaft, the tubular shaft having a thin portion which constitutes a distal side of the shaft, a thick portion which is provided further on a proximal side than the thin portion and has a larger outer diameter than that of the thin portion, and a tapered portion which constitutes a portion from a proximal end of the thin portion to a distal end of the thick portion and of which the outer diameter is reduced toward the distal side; the tapered portion is formed more flexibly than the thick portion; the thick portion has a first thick portion and a second thick portion which is provided between the tapered portion and the first thick portion; and the second thick portion has a smaller outer diameter than the outer diameter of a proximal end of the tapered portion and the outer diameter of the first thick portion, and is formed more flexibly than the first thick portion.

In accordance with an exemplary embodiment, the second thick portion which has a smaller outer diameter than the tapered portion and the first thick portion is provided between the tapered portion and the first thick portion, and therefore, flexibility can be smoothly changed (or transitioned) from the tapered portion to the thick portion. Accordingly, a pushing force can be easily and smoothly transmitted from the operator side to the distal side, which can improve operability.

In the aforesaid catheter, the shaft may have an inner layer and an outer layer which is provided outside the inner layer, and the outer diameter of the outer layer in the second thick portion may be smaller than that of the outer layer in the first thick portion. According to this configuration, the flexibility from the second thick portion to the first thick portion can be changed.

In the aforesaid catheter, the hardness of a material constituting the outer layer in the first thick portion may be the same as that of a material constituting the outer layer in the second thick portion. According to this configuration, the flexibility from the second thick portion to the first thick portion can be changed.

In the aforesaid catheter, the hardness of a material constituting the outer layer in the tapered portion is lower than that of a material constituting the outer layer in the second thick portion. According to this configuration, the flexibility from the tapered portion to the second thick portion can be changed.

In accordance with an exemplary embodiment, a catheter is disclosed, comprising: a tubular shaft, the tubular shaft having a distal portion and a proximal portion, the distal portion constitutes a distal side of the shaft, the proximal portion being on a proximal side of the distal portion and having a larger outer diameter than that of the distal portion, and a tapered portion extending from a proximal end of the distal portion to a distal end of the proximal portion and of which an outer diameter of the tapered portion is reduced towards the distal side of the shaft; the tapered portion being more flexible than the proximal portion; the proximal portion having a first portion and a second portion, the second portion being between the tapered portion and the first portion; and the second portion having a smaller outer diameter than an outer diameter of a proximal end of the tapered portion and an outer diameter of the first portion, and the second portion being more flexible than the first portion.

DETAILED DESCRIPTION

Hereinafter, a catheter according to the present disclosure will be described with reference to the accompanying drawings using preferred embodiments.

Figure 1:
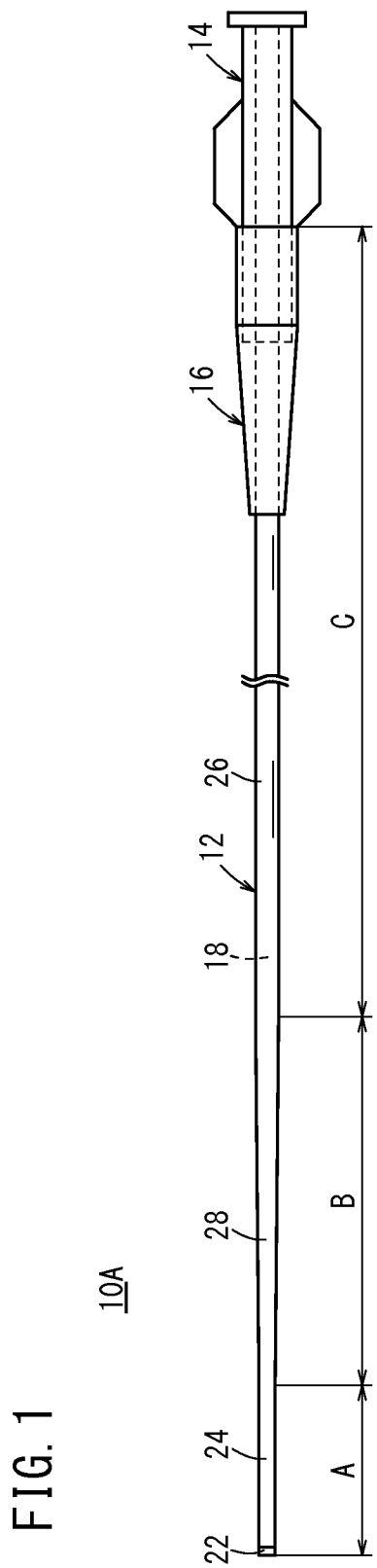
FIG. 1 is a side surface view of a catheter according to a first embodiment of the present disclosure.
Figure 2:
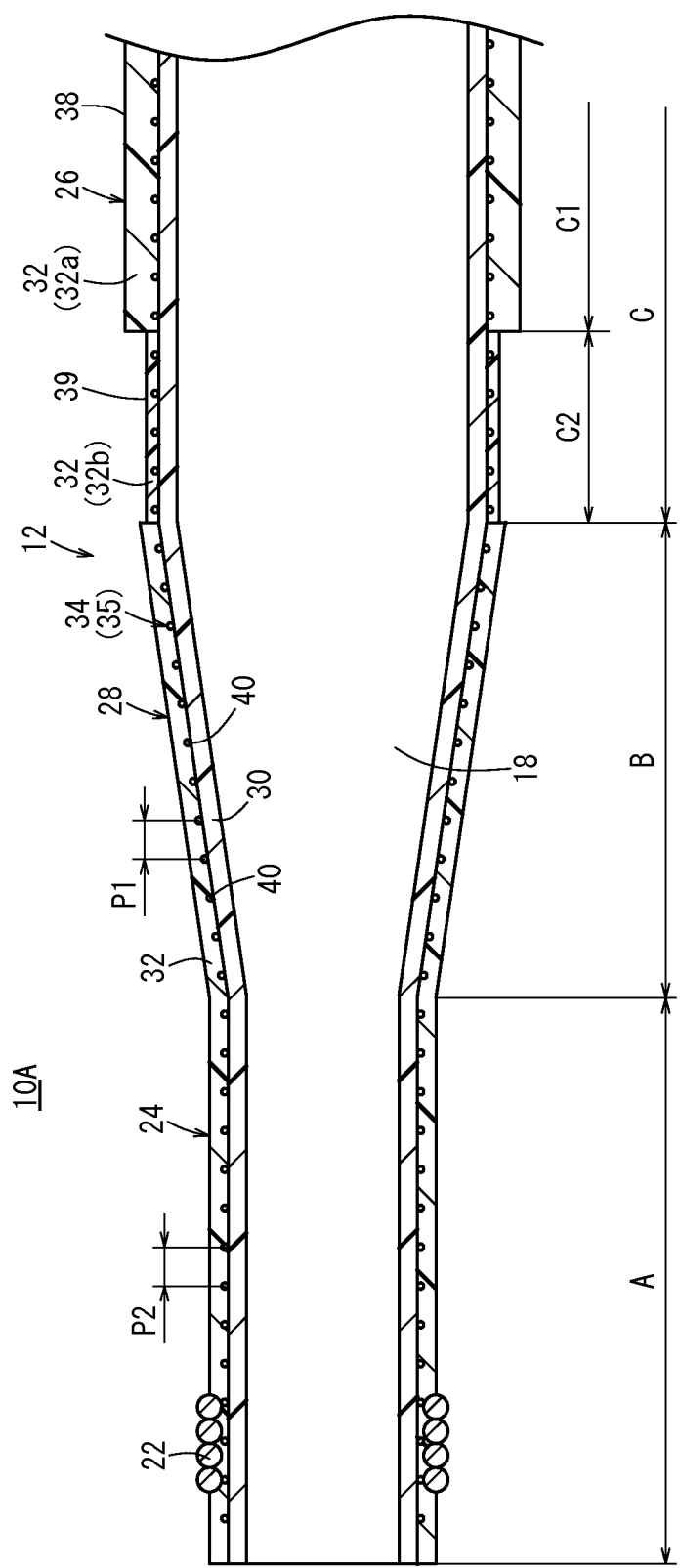
FIG. 2 is a longitudinal cross-sectional view showing a configuration of the catheter on a distal portion shown in FIG. 1.

FIG. 1 is a side surface view of a catheter 10A according to a first embodiment of the present disclosure. FIG. 2 is a longitudinal cross-sectional view showing a configuration of the catheter 10A on a distal portion side. Note that FIG. 2 shows a schematic shape of a shaft 12, and therefore, the dimensional ratio of the outer diameter to the length thereof is not always coincident with the shaft 12 shown in FIG. 1.

The catheter 10A can be used for, for example, injecting a medicine for treatment or injecting a contrast agent for diagnosis by being inserted into a blood vessel or a lumen in a living body and making a distal end of the catheter reach a target part. As shown in FIG. 1, the catheter 10A includes an elongated shaft 12 with a thin diameter, a hub 14, which is connected to a proximal end of the shaft 12, and a strain relief 16 which is provided in a connection portion to the hub 14 of the shaft 12.

Note that, in the following description, in relation to the shaft 12, the side of the hub 14 is also called a proximal side and the side, which is opposite to the side to which the hub 14 is connected is also called a distal side, and the same applies to other drawings.

The shaft 12 constitutes a main body of the catheter to be inserted into body lumens such as blood vessels, and is an elongated tubular member with a thin diameter in which a lumen 18 (also refer to FIG. 2) communicating between the distal end and the proximal end is formed and which has flexibility. The length of the shaft 12 can be, for example, about 500 mm to 2000 mm and preferably about 1000 mm to 1500 mm. The inner diameter and the outer diameter of the shaft 12 can vary depending on the position in an axial direction, and therefore, will be described later.

As shown in FIGS. 1 and 2, a radiopaque marker (contrast marker) 22 can be fixed onto an outer circumferential surface in the vicinity of the most distal portion of the shaft 12. The radiopaque marker 22 can be formed of a material, such as gold or platinum, which has radiopacity so as to visually check the position of the distal end of the catheter 10A in a living body under X-ray imaging.

In accordance with an exemplary embodiment, the radiopaque marker 22 in FIG. 2 is formed into a coil shape helically extending on the outer circumferential portion of the shaft 12, but may also be formed into a ring shape. In addition, the radiopaque marker 22 is not limited to having a configuration in which the radiopaque marker is embedded in a tube wall of the shaft 12, and may also be exposed to the outer circumferential surface. In accordance with an exemplary embodiment, the most distal portion of the shaft 12 may have a taper.

As shown in FIG. 1, the hub 14 holds the proximal end of the shaft 12 at the distal end of the hub, and is formed such that other instruments such as syringe can be connected to the proximal end of, the hub. The hub 14 can be formed of, for example, a hard resin such as polycarbonate, polyethylene, and polypropylene. The strain relief 16 is used for preventing the shaft 12 from being bent (kinked) at the connection portion to the hub 14 and is a resin member, which is formed into, for example, a tapering tubular shape and has flexibility and rigidity. The strain relief 16 can be formed of the same material as the constituent material of the shaft 12.

Next, a specific configuration of the shaft 12 will be described. As shown in FIGS. 1 and 2, the shaft 12 has a thin portion 24 which constitutes a distal side (range shown by an arrow A) of the shaft 12, a thick portion 26 which constitutes a portion (range shown by an arrow C) further on a proximal side than the thin portion 24 and has a larger outer diameter than that of the thin portion 24, and a tapered portion 28 which constitutes a portion (range shown by an arrow B) from a proximal end of the thin portion 24 to a distal end of the thick portion 26 and of which the outer diameter is reduced toward the distal side. The radiopaque marker 22 can be provided on the thin portion 24, and the thick portion 26 and the radiopaque marker 22 can exist independently from each other. That is, for example, a thick portion can be selected in which no marker exists as the thick portion 26.

Figure 3:
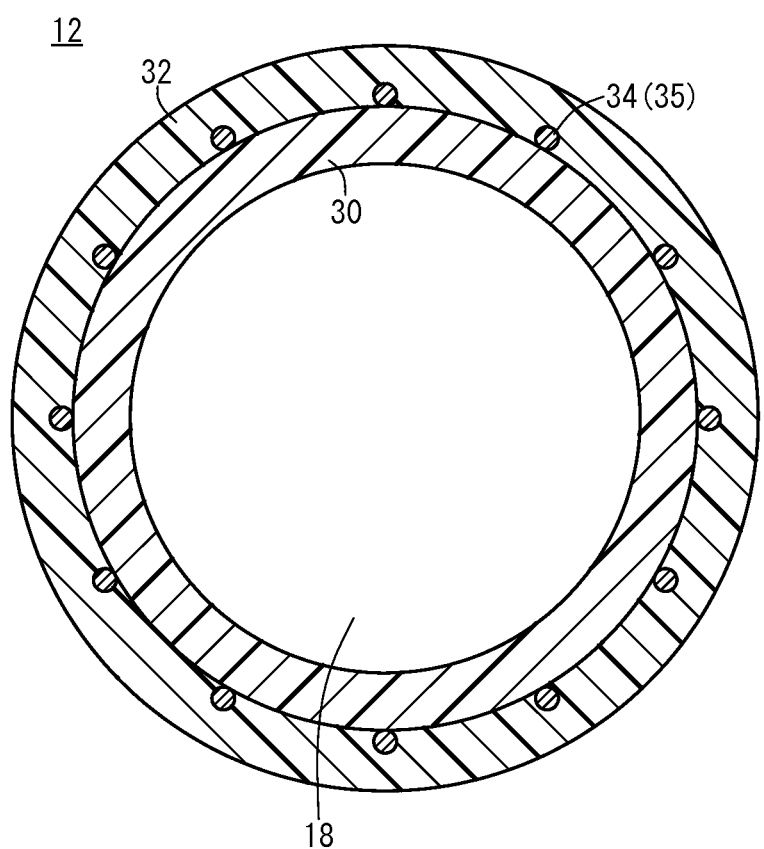
FIG. 3 is a transverse cross-sectional view of a shaft of the catheter shown in FIG. 1.

FIG. 3 is a transverse cross-sectional view of the shaft 12. As shown in FIG. 3, the shaft 12 has an inner layer 30 in which a lumen 18 is formed, an outer layer 32 which is formed on a radially outer side of the inner layer 30, and a reinforcement layer 34 which is formed along the outer circumference of the inner layer 30. In accordance with an exemplary embodiment, the inner layer 30 is seamlessly and continuously formed of an identical material over the whole length of the shaft 12. The reinforcement layer 34 is provided over the whole length of the shaft 12. In accordance with an exemplary embodiment, the reinforcement layer 34 may not be provided at the distal end of the shaft 12.

The inner layer 30 and the outer layer 32 can be formed of a synthetic resin having appropriate flexibility. Examples of the constituent material of the inner layer 30 include fluorine resins such as PFA (copolymer of tetrafluoroethylene and perfluoroalkoxyethylene) and PTFE (polytetrafluoroethylene).

Examples of the constituent material of the outer layer 32 can include polymer materials including polyolefin (for example, polyethylene, polypropylene, polybutene, ethylene-propylene copolymer, ethylene-vinyl acetate copolymer, ionomer, or a mixture of two or more of the materials mentioned above), polyvinyl chloride, polyamide, polyester, polyester elastomer, polyamide elastomer, polyurethane, polyurethane elastomer, polyimide, and fluorine resin, or a mixture of the materials mentioned above.

In accordance with an exemplary embodiment, the inner layer 30 and the outer layer 32 may also be formed of other materials. The cross-sectional shape of the inner layer 30 and the outer layer 32 in a natural state (i.e., state in which no external force is applied) is almost a circle.

In FIG. 2, the length of the thin portion 24 (portion of the shaft 12 in a range shown by an arrow A) in an axial direction of the shaft 12 is set to, for example, about 3 mm to 300 mm and preferably to about 10 mm to 150 mm. The inner diameter and the outer diameter of the inner layer 30 in the thin portion 24 are constant over the whole length of the thin portion 24. The inner diameter and the outer diameter of the outer layer 32 in the thin portion 24 are constant over the whole length of the thin portion 24.

The inner diameter of the inner layer 30 in the thin portion 24 can be set to, for example, about 0.2 mm to 2.5 mm and preferably to about 0.3 mm to 1.8 mm. The outer diameter of the outer layer 32 in the thin portion 24 is set to, for example, about 0.3 mm to 3.0 mm and preferably to about 0.4 mm to 2.0 mm.

The length of the tapered portion 28 (portion of the shaft 12 in a range shown by an arrow B) in the axial direction of the shaft 12 can be set to, for example, about 5 mm to 500 mm and preferably to about 10 mm to 100 mm. The outer diameter of the distal end of the outer layer 32 in the tapered portion 28 is the same as that of the thin portion 24. The inner diameter of the inner layer 30 in the tapered portion 28 is coincident with the inner diameter of the inner layer 30 in the thin portion 24 on the distal side and is coincident with the inner diameter of the inner layer 30 in the thick portion 26 on the proximal side, and the inner diameter between the tapered portion on the distal side and the tapered portion on the proximal side is reduced at a constant ratio toward the side of the thin portion 24.

In accordance with an exemplary embodiment, the wall thicknesses of the inner layer 30 and the outer layer 32 in the tapered portion 28 are respectively constant over the whole length of the tapered portion 28. In the illustrated example, the outer layer 32 can be seamlessly and continuously formed of an identical material over the whole length of the thin portion 24 and the tapered portion 28 from the distal end of the thin portion 24 to the proximal end of the tapered portion 28. Accordingly, the thickness of the outer layer 32 in the tapered portion 28 can be constant over the whole length of the tapered portion 28, and the outer layer 32 can be seamlessly and continuously formed of an identical material. That is, for example, the outer layer 32 in the tapered portion 28 is not formed such that a plurality of members are connected to each other in the axial direction, and is formed without seams (seamless) in the middle of the outer layer.

The length of the thick portion 26 (portion of the shaft 12 in a range shown by an arrow C) in the axial direction of the shaft 12 can be set to for example, about 200 mm to 1800 mm and preferably to about 400 mm to 1500 mm. The inner diameter and the outer diameter of the inner layer 30 in the thick portion 26 are constant over the whole length of the thick portion 26. The inner diameter of the inner layer 30 in the thick portion 26 can be set to, for example, about 0.3 mm to 9.0 mm and preferably to about 0.4 mm to 2.8 mm.

In the illustrated example, the thick portion 26 has a first thick portion 38 and a second thick portion 39 which is provided on a distal side of the first thick portion 38. In accordance with an exemplary embodiment, the first thick portion 38 constitutes a portion (portion of the shaft 12 in a range shown by an arrow C1) from the vicinity (further on a proximal side slightly than a proximal end of the tapered portion 28) of a distal end of the thick portion 26 of the shaft 12 to a proximal end of the thick portion 26 of the shaft 12. The outer diameter of the first thick portion 38 is constant over the whole length of the first thick portion 38 and can be set to, for example, about 0.4 mm to 10.0 mm and preferably to about 0.5 mm to 3.0 mm.

An outer layer 32a in the first thick portion 38 may be formed such that a plurality of materials with different hardness are arranged in the axial direction. In the illustrated example, the outer layer 32a in the first thick portion 38 has a plurality of areas with different hardness along the axial direction, and the hardness of the materials constituting each area is decreased toward the distal side (whereas flexibility is increased toward the distal side).

The second thick portion 39 constitutes a portion (portion of the shaft 12 in a range shown by an arrow C2) of the shaft 12 between the tapered portion 28 and the first thick portion 38. The second thick portion 39 has a smaller outer diameter than the outer diameter of the proximal end of the tapered portion 28 and the outer diameter of the first thick portion 38, and can be formed to be more flexible than the first thick portion 38. The distal end of an outer layer 32b in the second thick portion 39 is connected to the proximal end of the outer layer 32 in the tapered portion 28 and the proximal end of the outer layer 32b in the second thick portion 39 is connected to the distal end of the outer layer 32b in the first thick portion 38.

The outer diameter of the outer layer 32b in the second thick portion 39 is set to be smaller than that of the outer layer 32a in the first thick portion 38, and for example, can be set to about 60% to 98% with respect to the first thick portion 38 and preferably to about 80% to 96% with respect to the first thick portion 38.

The hardness of the material constituting the outer layer 32a in the first thick portion 38 is the same as that of the material constituting the outer layer 32b in the second thick portion 39. However, the second thick portion 39 can be formed to be more flexible than the first thick portion 38 since the outer diameter of the outer layer 32b in the second thick portion 39 is smaller than that of the outer layer 32a in the first thick portion 38.

In accordance with an exemplary embodiment, the hardness of a material constituting the outer layer 32 in the tapered portion 28 can be lower than that of the material constituting the outer layer 32b in the second thick portion 39. Accordingly, the tapered portion 28 can be formed to be more flexible than the first thick portion 38.

Figure 4:
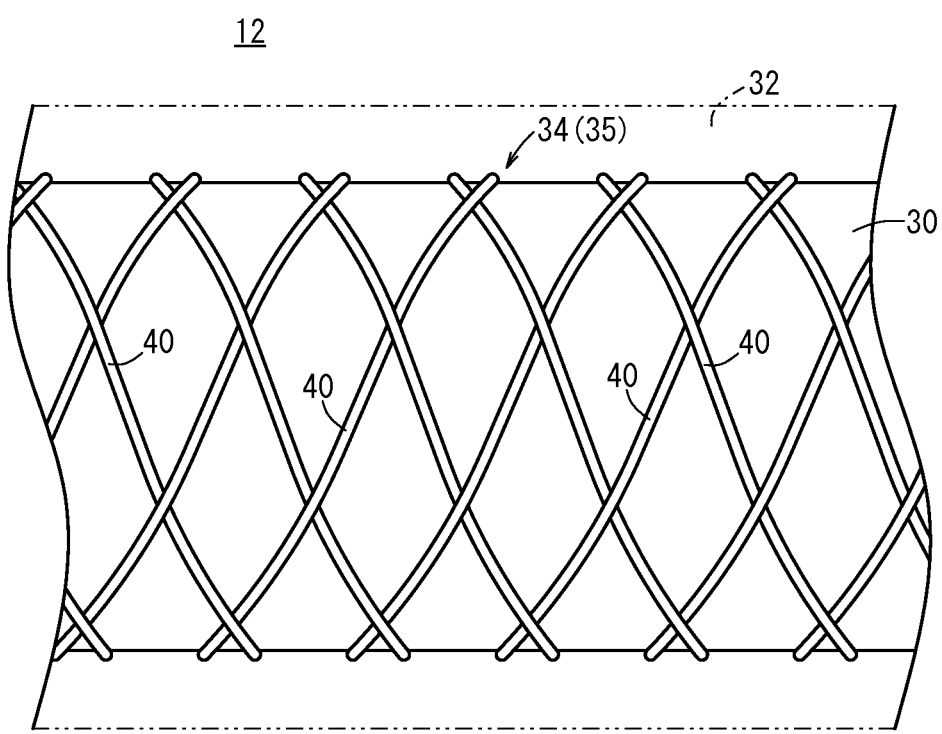
FIG. 4 is a view showing a configuration of a reinforcement layer which is provided on the shaft of the catheter shown in FIG. 1.

FIG. 4 is a view showing a configuration of the reinforcement layer 34 which is provided on the shaft 12, and shows the outer layer 32 using a virtual line for understanding of the configuration of the reinforcement layer 34 which is provided along the outer circumference of the inner layer 30. As shown in FIG. 4, the reinforcement layer 34 is formed of a braid 35 with a mesh pattern in which thin wires are weaved. In accordance with an exemplary embodiment, for example, the braid 35 can include a plurality of wires 40 wound in a first helical direction with set intervals from each other in the axial direction of the shaft 12, and a plurality of wires 40 wound in a second helical direction, which is different from the first helical direction, with set intervals from each other in the axial direction of the shaft 12 and which are arranged to intersect each other.

Examples of the constituent material of the wires 40 constituting the braid 35 include metal, a polymer, a composite of metal and a polymer, metal alloy (for example, stainless steel), or a combination thereof. The number of turns of the wires 40 wound in the first helical direction and the number of turns of the wires 40 wound in the second helical direction may be the same as or different from each other. The material, the thickness, or the cross-sectional shape of the wires 40 wound in the first helical direction and the material, the thickness, or the cross-sectional shape of the wires 40 wound in the second helical direction may be the same as or different from each other.

As shown in FIG. 2, a pitch P1 (arrangement interval in the axial direction of the wires 40) of the plurality of wires 40 constituting the reinforcement layer 34 in the tapered portion 28, along the axial direction of the shaft 12 is constant over the whole length of the tapered portion 28. In addition, a pitch P2 of the plurality of wires 40 constituting the reinforcement layer 34 in the thin portion 24, along the axial direction of the shaft 12 is constant over the whole length of the thin portion 24, and is the same as the pitch P1 of the reinforcement layer 34 in the tapered portion 28.

Next, the action and the effect of the catheter 10A which is constituted as described above will be described. In the catheter 10A, the second thick portion 39 which has a smaller outer diameter than the tapered portion 28 and the first thick portion 38 is provided between the tapered portion 28 and the first thick portion 38, and therefore, the flexibility from the tapered portion 28 to the thick portion 26 can be smoothly changed. That is, for example, in a case where the hardness of the material constituting the outer layer 32 in the tapered portion 28 is lower than the hardness of the material constituting the outer layer 32b in the second thick portion 39, if the outer diameter of the proximal end of the tapered portion 28 and the outer diameter of the second thick portion 39 are the same as each other, flexibility of the shaft 12 at a connection part between the tapered portion 28 and the second thick portion 39 can be changed. In contrast, as shown in the configuration of the catheter 10A, the change in the flexibility of the shaft 12 at the connection part between the tapered portion 28 and the second thick portion 39 can be reduced by reducing the outer diameter of the outer layer 32b in the second thick portion 39 so as to be smaller than the outer diameter of the proximal end of the outer layer 32 in the tapered portion 28. Therefore, according to the catheter 10A, a pushing force can be easily and smoothly transmitted from the operator side to the distal side to improve operability.

In addition, in the catheter 10A, the thickness of the outer layer 32 in the tapered portion 28 can be constant over the whole length of the tapered portion 28, and the outer layer 32 can be seamlessly and continuously formed of an identical material. Therefore, the flexibility toward the distal side of the shaft 12 can be smoothly changed. That is, for example, because the thickness of the outer layer 32 in the tapered portion 28 is constant and seamless, there is no part at which the flexibility (hardness) is steeply (or rapidly) changed, and the flexibility is smoothly increased as the outer diameter of the outer layer in the tapered portion is reduced toward the distal side. Therefore, according to the catheter 10A, a pushing force can be easily and smoothly transmitted from the operator side to the distal side.

Furthermore, in the catheter 10A, the pitch P1 (refer to FIG. 2) of the plurality of wires 40 constituting the reinforcement layer 34 in the tapered portion 28, along the axial direction of the shaft 12 is constant over the whole length of the tapered portion 28. According to this configuration, in the tapered portion 28, influence of the reinforcement layer 34 on the change in flexibility can be eliminated by eliminating change in the pitch of the reinforcement layer 34. Accordingly, the configuration is disclosed in which flexibility is smoothly changed along the axial direction since the flexibility is changed along the axial direction based on the change in the outer diameter of the outer layer 32.

Figure 5:
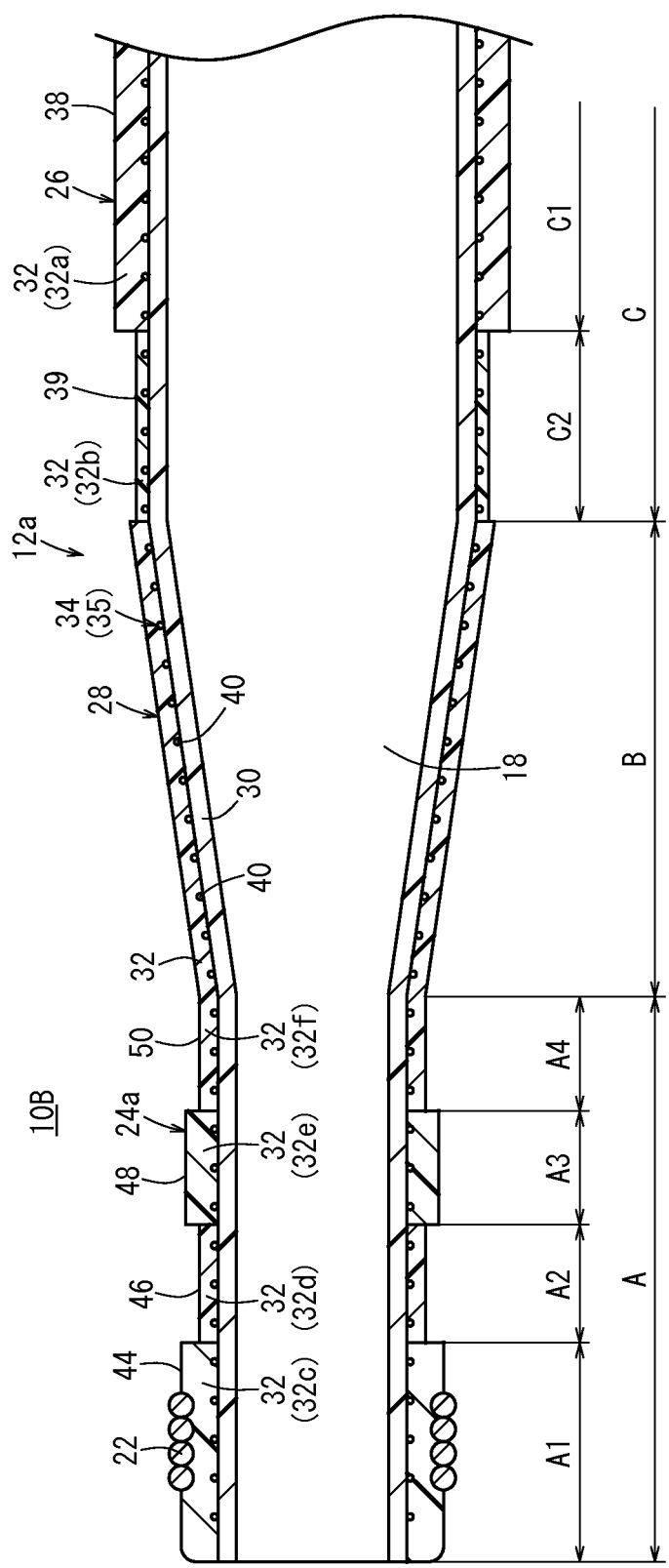
FIG. 5 is a longitudinal cross-sectional view showing a configuration of a distal portion of a catheter according to a second embodiment of the present disclosure.

FIG. 5 is a longitudinal cross-sectional view showing a configuration of a distal portion of a catheter 10B according to a second embodiment of the present disclosure. Note that, in the catheter 10B according to the present embodiment, elements exhibiting the same or equivalent function or effect as that of the above-described catheter 10A will be given the same reference numerals and the detailed description thereof will not be repeated. In addition, although a proximal side of the catheter 10B is not shown in FIG. 5, the proximal side of the catheter 10B is constituted similarly to the catheter 10A shown in FIG. 1.

A shaft 12a of the catheter 10B has a thin portion 24a which constitutes a distal side of the shaft 12a, a thick portion 26 which is provided further on a proximal side than the thin portion 24a and has a larger outer diameter than that of the thin portion 24a, and a tapered portion 28 which constitutes a portion from a proximal end of the thin portion 24a to a distal end of the thick portion 26 and of which the outer diameter is reduced toward the distal side. The thick portion 26 and the tapered portion 28 in the shaft 12a are configured similarly to the thick portion 26 and the tapered portion 28 in the shaft 12 shown in FIG. 2.

As shown in FIG. 5, the thin portion 24a has a first area 44 (portion of the shaft 12 in a range shown by an arrow A1) constituting the most distal portion of the shaft 12a in the present embodiment, a second area 46 (portion of the shaft 12 in a range shown by an arrow A2) which is adjacent to a proximal side of the first area 44 and has a smaller outer diameter than that of the first area 44, a third area 48 (portion of the shaft 12 in a range shown by an arrow A3: second thin portion) which is adjacent to a proximal side of the second area 46 and has a larger outer diameter than that of the second area 46, and a fourth area 50 (portion of the shaft 12 in a range shown by an arrow A4: first thin portion) which is adjacent to a proximal side of the third area 48 and has a smaller outer diameter than that of the third area 48.

The outer diameter of an outer layer 32c in the first area 44 can be set to, for example, about 0.3 mm to 3.0 mm and preferably to about 0.4 mm to 2.0 mm. The length of the outer layer 32c in the first area 44 along an axial direction of the shaft 12 can be set to, for example, about 0.5 mm to 50.0 mm and preferably to about 2.0 mm to 30.0 mm.

The outer diameter of an outer layer 32d in the second area 46 can be set to, for example, about 80% to 99% with respect to the outer layer 32c and preferably to about 85% to 98% with respect to the outer layer 32c. The length of the outer layer 32d in the second area 46 along the axial direction of the shaft 12 can be set to, for example, about 0.5 mm to 50.0 mm and preferably to about 2.0 mm to 30.0 mm.

The outer diameter of an outer layer 32e in the third area 48 can be set to, for example, about 101% to 130% with respect to the outer layer 32d and preferably to about 102% to 115% with respect to the outer layer 32d. The length of the outer layer 32e in the third area 48 along the axial direction of the shaft 12 can be set to, for example, about 0.5 mm to 50.0 mm and preferably to about 2.0 mm to 30.0 mm.

The outer diameter of an outer layer 32f in the fourth area 50 can be set to, for example, about 80% to 99% with respect to the outer layer 32e and preferably to about 85% to 98% with respect to the outer layer 32e. The length of the outer layer 32f in the fourth area 50 along the axial direction of the shaft 12 can be set to, for example, about 1.5 mm to 150.0 mm and preferably to about 4.0 mm to 60.0 mm.

In accordance with an exemplary embodiment, the first area 44 is formed more flexibly than the second area 46. In accordance with an exemplary embodiment, for example, the outer diameter of the outer layer 32c in the first area 44 is larger than that of the outer layer 32d in the second area 46. However, the hardness of a material constituting the outer layer 32c in the first area 44 can be set to be lower than that of a material constituting the outer layer 32d in the second area 46. Accordingly, the first area 44 is formed more flexibly than the second area 46.

In accordance with an exemplary embodiment, the second area 46 can be formed to be more flexible than the third area 48. In accordance with an exemplary embodiment, for example, the hardness of the material constituting the outer layer 32d in the second area 46 is the same as that of a material constituting the outer layer 32e in the third area 48. However, the outer diameter of the outer layer 32d in the second area 46 can be set to be smaller than that of the outer layer 32e in the third area 48. Accordingly, the second area 46 can be formed to be more flexible than the third area 48.

The third area 48 can be formed to be more flexible than the fourth area 50. For example, the outer diameter of the outer layer 32e in the third area 48 is larger than that of the outer layer 32f in the fourth area 50. However, the hardness of a material constituting the outer layer 32e in the third area 48 can be set to be lower than that of a material constituting the outer layer 32f in the fourth area 50. Accordingly, the third area 48 can be formed to be more flexible than the fourth area 50.

Next, the action and the effect of the catheter 10B according to the present embodiment which is constituted as described above will be described.

In the case of the present embodiment, in the thin portion 24a constituting the distal side of the shaft 12a, the second area 46 is provided between the first area 44 and the third area 48 so as to have a reduced outer diameter with respect to the front and rear thereof; and the thin portion 24a is constituted such that flexibility increases in the order of the third area 48, the second area 46, and the first area 44. For this reason, in the distal side of the shaft 12a, a configuration is disclosed in which flexibility increases toward the portion on the distal side and the flexibility is smoothly changed along the axial direction.

In addition, in the shaft 12a, flexibility is changed at a connection part between the first area 44 and the second area 46 and at a connection part between the second area 46 and the third area 48. The shaft 12a is easily bent at a part at which flexibility is changed. Therefore, the distal portion of the shaft 12a more smoothly and easily follows the bending of the body lumen such as the blood vessel by providing a plurality of change points of flexibility further on the distal side than the tapered portion 28.

Therefore, according to the catheter 10B, flowability and accessibility can be enhanced with respect to the peripheral blood vessel by providing the distal portion of the shaft 12a with sufficient flexibility and to smoothly transmit pushing force from the operator side to the distal side, and therefore, it is possible to enhance operability.

In addition, in the case of the present embodiment, the outer diameter of the outer layer 32d in the second area 46 is smaller than that of the outer layer 32c in the first area 44, the outer diameter of the outer layer 32e in the third area 48 is larger than that of the outer layer 32d in the second area 46, and the hardness of the material constituting the outer layer 32c in the first area 44 is lower than that of the material constituting the outer layers 32d and 32e in the second area 46 and the third area 48. According to this configuration, flexibility is changed in accordance with the difference in the outer diameter of the outer layer 32, that is, the difference in the cross-sectional area of the outer layer 32, and the difference in the hardness of the material constituting the outer layer 32. Therefore, a configuration is disclosed in which flexibility is smoothly changed.

Furthermore, in the case of the present embodiment, the hardness of the material constituting the outer layer 32d in the second area 46 can be the same as the hardness of the material constituting the outer layer 32e in the third area 48. According to this configuration, flexibility is changed by differentiating the outer diameter between the second area 46 and the third area 48 while making the hardness of the outer layer 32 of the second area 46 and the hardness of the outer layer 32 of the third area 48 the same as each other. Accordingly, the flexibility of each area can be set relatively easily, and therefore, it is possible to favorably obtain the configuration in which the flexibility is smoothly changed.

In the case of the present embodiment, the fourth area 50 (first thin portion) is connected to the distal end of the tapered portion 28 of which the outer diameter is reduced toward the distal side, and the third area 48 (second thin portion) which is more flexible than the fourth area 50, but of which the outer diameter is larger than the fourth area 50 is provided on the distal side of the fourth area 50. For this reason, in the distal side of the shaft 12a, a configuration is disclosed in which flexibility increases toward the portion on the distal side and the flexibility is smoothly changed. Therefore, according to the catheter 10B, flowability and accessibility can be enhanced with respect to the peripheral blood vessel and to relatively easily and smoothly transmit a pushing force from the operator side to the distal side.

In the case of the present embodiment, the outer diameter of the outer layer 32e in the third area 48 is larger than that of the outer layer 32f in the fourth area 50. However, the hardness of the material constituting the outer layer 32e in the third area 48 is lower than that of the material constituting the outer layer 32f in the fourth area 50. Accordingly, the third area 48 can be formed to be more flexible than the fourth area 50. According to this configuration, flexibility is changed in accordance with the difference in the outer diameter of the outer layer 32, that is, the difference in the cross-sectional area of the outer layer 32, and the difference in the hardness of the material. Therefore, the configuration is disclosed in which flexibility is smoothly changed along the axial direction.

Note that, in the catheter 10B according to the second embodiment, it is natural that it is possible to obtain the same action and effect as those of the catheter 10A in regard to constituent portions in common with the catheter 10A according to the first embodiment.

The detailed description above describes a catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter, comprising:
a tubular shaft having a seamless and continuous inner layer and an outer layer which is provided outside the inner layer, the tubular shaft including a thin portion which constitutes a distal side of the shaft, a thick portion which is provided further on a proximal side than the thin portion and having a larger outer diameter than an outer diameter of the thin portion, and a tapered portion which constitutes a portion from a proximal end of the thin portion to a distal end of the thick portion and an outer diameter of the tapered portion is reduced towards the distal side of the shaft;
the tapered portion is formed more flexibly than the thick portion;
the thick portion having a first thick portion and a second thick portion, the second thick portion extending from a proximal end of the tapered portion to a distal end of the first thick portion, and wherein the second thick portion has a length with an outer diameter forming a cylinder;

wherein the outer diameter of the second thick portion is smaller than an outer diameter of the proximal end of the tapered portion and an outer diameter of the first thick portion, and the second thick portion is formed more flexibly than the first thick portion; and wherein the thin portion comprises:
a first area constituting a most distal portion of the shaft;
a second area, which is adjacent to a proximal side of the first area and having a smaller outer diameter than that of the first area;
a third area, which is adjacent to a proximal side of the second area and having a larger outer diameter than that of the second area; and
a fourth area, which is adjacent to a proximal side of the third area and having a smaller outer diameter than that of the third area.

2. The catheter according to claim 1, wherein an outer diameter of an outer layer in the second thick portion is smaller than that of an outer layer in the first thick portion.

3. The catheter according to claim 2, wherein a hardness of a material constituting the outer layer in the first thick portion is equal to a hardness of a material constituting the outer layer in the second thick portion.

4. The catheter according to claim 3, wherein a hardness of a material constituting the outer layer in the tapered portion is lower than that of a material constituting the outer layer in the second thick portion.

5. The catheter according to claim 2, wherein a hardness of a material constituting the outer layer in the tapered portion is lower than that of a material constituting the outer layer in the second thick portion.

6. The catheter according to claim 1, comprising:
a radiopaque marker fixed onto an outer circumferential surface of a most distal portion of the shaft.

7. The catheter according to claim 1, wherein the outer layer comprises:
a reinforcement layer which is formed along an outer circumference of the inner layer.

8. The catheter according to claim 7, wherein the reinforcement layer is formed of a braid comprising a plurality of first wires wound in a first helical direction with set intervals from each other in an axial direction of the shaft, and a plurality of second wires wound in a second helical direction, which is different from the first helical direction, with set intervals from each other in the axial direction of the shaft and which are arranged to intersect each other.

9. The catheter according to claim 1, wherein
an outer diameter of an outer layer in the second area is smaller than that of an outer layer in the first area;
an outer diameter of an outer layer in the third area is larger than that of the outer layer in the second area; and
a hardness of a material constituting the outer layer in the first area is lower than that of a material constituting the outer layers in the second area and the third area.

10. The catheter according to claim 9, wherein a hardness of the material constituting the outer layer in the second area and a hardness of the material constituting the outer layer in the third area are equal.

11. A catheter, comprising:
a tubular shaft having a seamless and continuous inner layer and an outer layer which is provided outside the inner layer, the tubular shaft having a distal portion and a proximal portion, the distal portion constitutes a distal side of the shaft, the proximal portion being on a proximal side of the distal portion and having a larger outer diameter than an outer diameter of the distal portion, and a tapered portion extending from a proximal end of the distal portion to a distal end of the proximal portion and of which an outer diameter of the tapered portion is reduced towards the distal side of the shaft;
the tapered portion being more flexible than the proximal portion;
the proximal portion having a first portion and a second portion, the second portion extending from a proximal end of the tapered portion to a distal end of the first portion, and wherein the second portion has a length with an outer diameter forming a cylinder;
wherein the outer diameter of the second portion is smaller than an outer diameter of the proximal end of the tapered portion and an outer diameter of the first portion, and the second portion being more flexible than the first portion; and
wherein the distal portion comprises:
a first area constituting a most distal portion of the shaft;
a second area, which is adjacent to a proximal side of the first area and having a smaller outer diameter than that of the first area;
a third area, which is adjacent to a proximal side of the second area and having a larger outer diameter than that of the second area; and
a fourth area, which is adjacent to a proximal side of the third area and having a smaller outer diameter than that of the third area.

12. The catheter according to claim 11, wherein an outer diameter of an outer layer in the second portion is smaller than an outer layer in the first portion.

13. The catheter according to claim 12, wherein a hardness of a material constituting the outer layer in the first portion is equal to a hardness of a material constituting the outer layer in the second portion.

14. The catheter according to claim 12, wherein a hardness of a material constituting the outer layer in the tapered portion is lower than that of a material constituting the outer layer in the second portion.

15. The catheter according to claim 11, wherein the outer layer comprises:
a reinforcement layer which is formed along an outer circumference of the inner layer, and wherein the reinforcement layer is formed of a braid comprising a plurality of first wires wound in a first helical direction with set intervals from each other in an axial direction of the shaft, and a plurality of second wires wound in a second helical direction, which is different from the first helical direction, with set intervals from each other in the axial direction of the shaft and which are arranged to intersect each other.

16. The catheter according to claim 11, wherein
an outer diameter of an outer layer in the second area is smaller than that of an outer layer in the first area;
an outer diameter of an outer layer in the third area is larger than that of the outer layer in the second area; and
a hardness of a material constituting the outer layer in the first area is lower than that of a material constituting the outer layers in the second area and the third area.

17. The catheter according to claim 16, wherein a hardness of the material constituting the outer layer in the second area and a hardness of the material constituting the outer layer in the third area are equal.

18. A catheter, comprising:
a tubular shaft, the tubular shaft including a thin portion which constitutes a distal side of the shaft, a thick portion which is provided further on a proximal side than the thin portion and having a larger outer diameter than an outer diameter of the thin portion, and a tapered portion which constitutes a portion from a proximal end of the thin portion to a distal end of the thick portion and of which an outer diameter of the tapered portion is reduced towards the distal side of the shaft;
the tapered portion is formed more flexibly than the thick portion;
the thick portion having a first thick portion and a second thick portion, the second thick portion extending from a proximal end of the tapered portion to a distal end of the first thick portion, and wherein an outer diameter of the second thick portion is constant over an entire length of the second thick portion; and
the outer diameter of the second thick portion is smaller than an outer diameter of the proximal end of the tapered portion and an outer diameter of the first thick portion, and the second thick portion is formed more flexibly than the first thick portion.

* * * * *